US012636003B2

(12) United States Patent
Gersch et al.

(10) Patent No.: US 12,636,003 B2
(45) Date of Patent: May 26, 2026

(54) PERIANAL FISTULA CLOSURE SYSTEM

(71) Applicants: The Johns Hopkins University, Baltimore, MD (US); Baxter International Inc., Deerfield, IL (US); Baxter Healthcare SA, Opfikon (CH)

(72) Inventors: Kiley Gersch, Baltimore, MD (US); Sophia Diaz, Baltimore, MD (US); Karina Frank, Manassas, VA (US); Monet Slinowsky, Baltimore, MD (US); Ebenezer Adjei Armah, Baltimore, MD (US); Zachary Buono, Powhatan, VA (US); Youseph Yazdi, Ellicott City, MD (US); Evan Mosley, Berkley, MI (US); Russell Holscher, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 259 days.

(21) Appl. No.: 18/258,171

(22) PCT Filed: Dec. 2, 2021

(86) PCT No.: PCT/US2021/072693
§ 371 (c)(1),
(2) Date: Jun. 16, 2023

(87) PCT Pub. No.: WO2022/133387
PCT Pub. Date: Jun. 23, 2022

(65) Prior Publication Data
US 2024/0050082 A1     Feb. 15, 2024
Related U.S. Application Data
(60) Provisional application No. 63/127,789, filed on Dec. 18, 2020.

(51) Int. Cl.
| | |
|---|---|
| *A61B 17/04* | (2006.01) |
| *A61B 17/06* | (2006.01) |
| *A61B 17/00* | (2006.01) |

(52) U.S. Cl.
CPC ..................... *A61B 17/0401* (2013.01); *A61B 2017/00004* (2013.01); *A61B 2017/00579* (2013.01);
(Continued)

(58) Field of Classification Search
CPC ...... A61B 17/0401; A61B 2017/00004; A61B 2017/00579; A61B 2017/00623;
(Continued)

(56) References Cited

U.S. PATENT DOCUMENTS 5,269,809 A * 12/1993 Hayhurst ........... A61B 17/0401
                                                          606/220
5,350,399 A * 9/1994 Erlebacher ......... A61B 17/0057
                                                          606/151
(Continued)

FOREIGN PATENT DOCUMENTS

WO   WO-2010028300 A1 *  3/2010  ......... A61B 17/0057
WO   WO-2010062743 A2 *  6/2010  ....... A61B 17/06109
(Continued)

*Primary Examiner* — Katherine M Shi
(74) *Attorney, Agent, or Firm* — Harrity & Harrity, LLP

(57) ABSTRACT
A system may include a delivery device configured to deploy a perianal fistula closure device and the perianal fistula closure device configured to close a perianal fistula. The delivery device may include a helical catheter. The perianal fistula closure device may include a cap, a suture comprising a plurality of uni-directional barbs, and an anchor connected to an end of the suture comprising a plurality of uni-directional quills.

21 Claims, 6 Drawing Sheets

(52) U.S. Cl.
CPC .............. *A61B 2017/00623* (2013.01); *A61B 2017/00641* (2013.01); *A61B 2017/0456* (2013.01); *A61B 2017/06076* (2013.01)

(58) Field of Classification Search
CPC .. A61B 2017/00641; A61B 2017/0456; A61B 2017/06076; A61B 17/06166; A61B 17/06109; A61B 2017/00615; A61B 2017/0412; A61B 2017/0437; A61B 2017/06052; A61B 2017/00663; A61B 2017/00676; A61B 2017/06176; A61B 17/0057
See application file for complete search history.

(56) References Cited

U.S. PATENT DOCUMENTS

| | | | | |
|---|---|---|---|---|
| 5,370,661 A | * | 12/1994 | Branch | A61F 2/0811 24/17 AP |
| 9,271,706 B2 | * | 3/2016 | Stopek | A61L 27/52 |
| 2007/0005041 A1 | * | 1/2007 | Frassica | A61B 1/00154 623/1.1 |
| 2007/0049971 A1 | * | 3/2007 | Chin | A61B 17/06166 606/232 |
| 2010/0042144 A1 | * | 2/2010 | Bennett | A61B 17/0401 606/213 |
| 2015/0119905 A1 | * | 4/2015 | Shluzas | A61B 17/0401 606/144 |
| 2020/0107932 A1 | * | 4/2020 | Rabito | A61B 17/06004 |

FOREIGN PATENT DOCUMENTS

| | | | | |
|---|---|---|---|---|
| WO | WO-2013062933 A1 | * | 5/2013 | A61B 17/0401 |
| WO | WO-2016019349 A1 | * | 2/2016 | A61B 17/0057 |
| WO | WO-2018224687 A1 | * | 12/2018 | A61B 17/0057 |

* cited by examiner

PERIANAL FISTULA CLOSURE SYSTEM

CROSS-REFERENCE TO RELATED APPLICATIONS

This application is a 371 national stage of PCT Application PCT/US2021/072693 filed on Dec. 2, 2021, entitled "PERIANAL FISTULA CLOSURE SYSTEM," which claims priority to U.S. Provisional Patent Application No. 63/127,789, filed on Dec. 18, 2020, both of which are hereby expressly incorporated by reference herein.

BACKGROUND

A perianal fistula is an abnormal connection or inflammatory tract between the anal canal and the surrounding perianal skin.

SUMMARY

In some implementations, a system includes a delivery device configured to deploy a perianal fistula closure device, comprising: a helical catheter; and the perianal fistula closure device configured to close a perianal fistula, comprising: a cap, a suture comprising a plurality of uni-directional barbs, and an anchor connected to an end of the suture comprising a plurality of unidirectional quills.

In some implementations, a perianal fistula closure device configured to close a perianal fistula includes a cap; a suture comprising a plurality of uni-directional barbs; and an anchor connected to an end of the suture comprising a plurality of uni-directional quills.

In some implementations, a delivery device configured to deploy a perianal fistula closure device includes a driving component; and a helical catheter connected to the driving component, wherein the helical catheter is configured to, prior to the delivery device deploying the perianal fistula closure device: hold a suture of the perianal fistula closure device within an interior portion of the helical catheter, and hold an anchor of the perianal fistula closure device at an end of the helical catheter such that an insertion point of the anchor protrudes from the end of the helical catheter.

DETAILED DESCRIPTION

Figure 1:
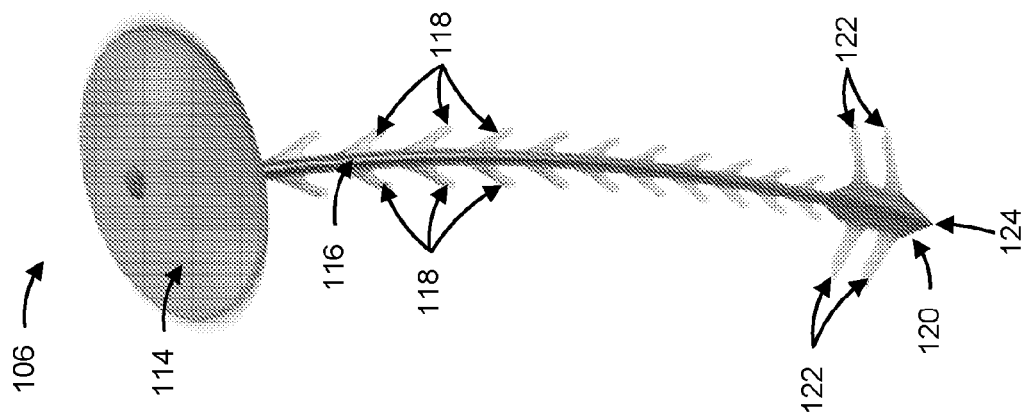
FIG. 1 is a diagram of an example system described herein.
Figure 1:
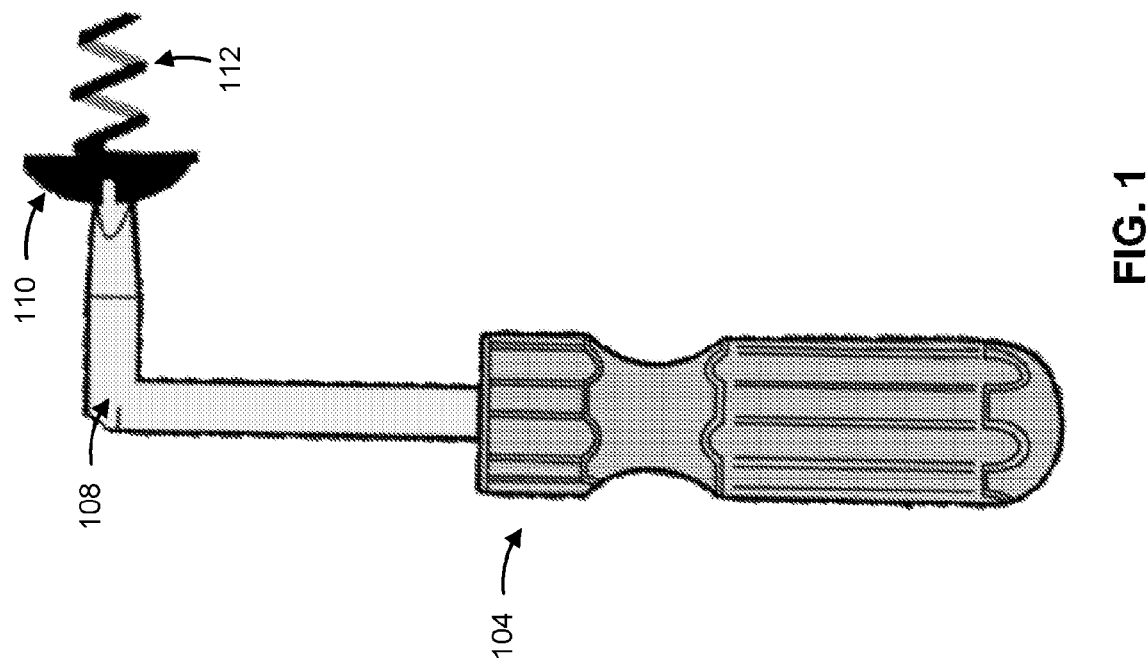
Figure 1:
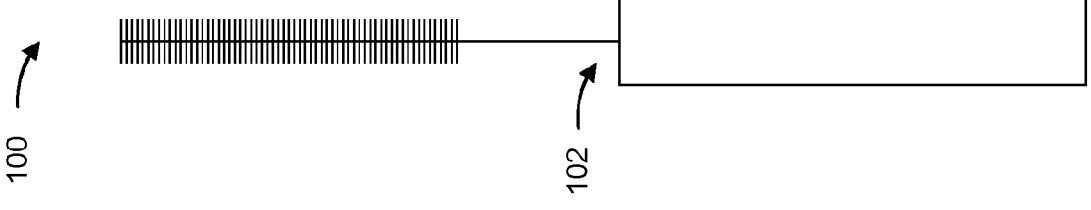

The following detailed description of example implementations refers to the accompanying drawings. The same reference numbers in different drawings may identify the same or similar elements.

A perianal fistula is a debilitating physical condition that affects 140,000 individuals annually in the U.S., and one in 5,000 people worldwide. A perianal fistula may cause symptoms such as pain and constant drainage, which may prevent a person from sitting or performing other daily tasks. This may severely degrade the person's quality of life. In some cases, if left untreated, a perianal fistula can lead to sepsis and death. Consequently, a person with a perianal fistula may suffer mentally as well as physically.

A perianal fistula may be classified as either simple or complex based on its anatomy and/or patient comorbidities. A simple perianal fistula, for example, may include a single tract or may be limited in size and therefore can be treated via a fistulotomy surgical procedure. A complex perianal fistula, for example, may have multiple or branching tracts or may be associated with more than one-third of an external anal sphincter muscle (e.g., a main muscle that controls fecal continence). Additionally, a perianal fistula may be considered complex if it is a recurrent perianal fistula or if a person with the perianal fistula suffers from an inflammatory bowel disease (IBD), such as Crohn's Disease.

Objectives of a complex perianal fistula treatment are to fully rid the perianal fistula tract of local infection, to close the perianal fistula tract, and to aid healing of tissue associated with the complex perianal fistula. If any of these objectives are not met, the complex perianal fistula may persist.

In some cases, a mucosal advancement flap procedure may be used to treat a complex perianal fistula. In this procedure, a surgeon harvests a patient's native mucosal tissue from an area surrounding a perianal fistula opening, stretches the mucosal tissue over the perianal fistula opening and sutures the mucosal tissue into place, thereby blocking the opening of the perianal fistula from infectious material entry and allowing for healing. However, this procedure requires substantial skill and is usually performed with minimal to no visibility of a small working area. Moreover, the procedure cannot be performed on inflamed, delicate tissue such as that of Crohn's disease patients. Accordingly, the mucosal advancement flap procedure as well as other conventional treatments, such as a fistulotomy, are only successful 40-70% of the time, with an average recurrence rate of 30%.

Consequently, many people repeatedly undergo painful treatments that often do not eliminate complex perianal fistulas. In addition, due to an anatomical location of a complex perianal fistula, a surgeon must take care to not harm a significant portion of a person's anal sphincter muscles. If a surgeon harms the anal sphincter muscles, the person may suffer from partial or complete fecal incontinence. Accordingly, a conventional treatment is often ineffective because the treatment fails to fully block or close a perianal fistula's internal opening, requires multiple procedures to complete the treatment, and/or fails to maintain patient fecal continence.

Some implementations described herein provide a system for treating a perianal fistula, such as a complex perianal fistula. The system may include a perianal fistula debriding device for cleaning and debriding the perianal fistula. The system may include a perianal fistula closure device that is configured to close the perianal fistula. The perianal fistula closure device may include a cap, a suture comprising a plurality of barbs, and an anchor that is attached to an end of the suture and that comprises a plurality of quills. The system may include a delivery device that is configured to insert the perianal fistula closure device in tissue surrounding the perianal fistula and to deploy the perianal fistula closure device to cause the perianal fistula to close. The delivery device may include a shaft, a driving component connected to an end of the shaft, and a helical catheter connected to the driving component.

In some implementations, the suture of the perianal fistula closure device may be configured to distribute around an outer circumference of the perianal fistula in a helix to collapse a lumen of the perianal fistula. The anchor of the perianal fistula closure device may be configured to implant into a sphincter muscle associated with the perianal fistula. The plurality of barbs of the suture and the plurality of quills of the anchor are configured to cause the suture to be secured when distributed around the perianal fistula and to be taut to facilitate closure of the perianal fistula and promote healing of tissue around the perianal fistula. The cap may be configured to cover an opening of the perianal fistula on a surface of an anal canal or a rectum and to prevent entry of foreign material into the perianal fistula via the opening. The suture, the anchor, and the cap may comprise a biocompatible material or a bioabsorbable material.

In some implementations, the helical catheter may be configured to hold the suture and the anchor of the perianal fistula closure device prior to insertion and deployment of the perianal fistula closure device into the tissue surround the perianal fistula. The helical catheter may hold the suture within an interior portion of the helical catheter and may hold the anchor at end of the helical catheter such that an insertion point of the anchor protrudes from the end of the helical catheter. The shaft and driving component of the delivery device may be configured to turn to cause the helical catheter (that holds the suture and the anchor of the perianal fistula closure device) to insert into the tissue surrounding the perianal fistula. The shaft and driving component of the delivery device may be configured to turn (e.g., in an opposite direction) to cause the anchor to release from the helical catheter and to implant into the sphincter muscle associated with the perianal fistula, to cause the suture to release from the helical catheter and to distribute in the helix around the perianal fistula; to cause the helical catheter to be removed from the tissue surrounding the perianal fistula; and to cause the suture to tighten as the helical catheter is removed, which facilitates closure of the perianal fistula.

In this way, some implementations described herein provide a perianal fistula closure device that closes a perianal fistula and blocks an opening of the perianal fistula, which facilitates end-to-end healing of the perianal fistula. The barbed suture and the quilled anchor of the perianal fistula closure device ensure that the suture remains distributed around the perianal fistula and that the cap is held over an opening of the perianal fistula for an amount of time (e.g., 4-6 weeks, or until the suture and/or the anchor are absorbed or dissolve) to allow the perianal fistula to heal, which reduces a likelihood of recurrence of the perianal fistula. Moreover, because the perianal fistula closure device utilizes a suture with a plurality of barbs and an anchor with a plurality of quills, the perianal fistula closure device is secured in place without a need for a surgeon to tie knots in the suture with little to no visualization.

Accordingly, a surgeon may use the delivery device to deploy the perianal fistula closure device instead of performing a complex surgical procedure, and may thereby reduce a likelihood of damaging a sphincter muscle in a way that impacts patient fecal continence. The delivery device also enables automated deployment of the helical catheter, the suture, and the anchor, to an appropriate diameter and depth to approximate tissue surrounding a perianal fistula, further reducing a complexity involved with closing the perianal fistula.

FIG. 1 is a diagram of an example system 100 described herein. As shown in FIG. 1, the system 100 may include a perianal fistula debriding device 102, a delivery device 104, and a perianal fistula closure device 106. The perianal fistula debriding device 102 may comprise a wire brush or any other similar type of device configured to clean and/or debride a perianal fistula (e.g., to remove epithelial tissue in a tract of the perianal fistula and/or to expose fresh tissue on the interior of the tract) and/or to stimulate healing of the perianal fistula (e.g., to damage tissue associated with the perianal fistula, which stimulates healing of the tissue and thereby promotes growth of the tissue to close the perianal fistula). The delivery device 104 may comprise a shaft 108, a driving component 110 connected to an end of the shaft 108, and/or a helical catheter 112 connected to the driving component 110. The perianal fistula closure device 106 may comprise a cap 114, a suture 116 comprising a plurality of barbs 118, and an anchor 120 connected to an end of the suture 116 comprising a plurality of quills 122 and an insertion point 124. The cap 114 may comprise a biocompatible material, such as polyurethane or a similar material. The suture 116, the plurality of barbs 118, the anchor 120, the plurality of quills 122, and/or the insertion point 124 may comprise a biocompatible material or bioabsorbable material, such as polydioxanone or a similar material. The suture 116 and/or the plurality of barbs 118 may comprise and/or be integrated with a therapeutic drug (e.g., that is configured to promote healing of the perianal fistula).

The delivery device 104 may be configured to insert the perianal fistula closure device 106 in tissue surrounding a perianal fistula and/or to deploy the perianal fistula closure device 106 to cause the perianal fistula to close. The helical catheter 112 may have an inner diameter that is greater than an outer diameter of the perianal fistula (e.g., greater than a maximum outer diameter of the tract of the perianal fistula). For example, the helical catheter 112 may have an outer diameter of 10-12 millimeters (mm), which is greater than an outer diameter of typical perianal fistulas, which typically have a maximum outer diameter of 5-6 mm. In some implementations, the helical catheter 112 (e.g., prior to insertion or deployment of the perianal fistula closure device 106) may hold the suture 116 and the anchor 120. For example, the helical catheter 112 may hold the suture 116 within an interior portion of the helical catheter 112 and may hold the anchor 120 at an end of the helical catheter 112 to allow the insertion point 124 of the anchor 120 to protrude from the end of the helical catheter 112 (e.g., as further described herein in relation to FIG. 3A). The anchor 120 may have a diameter that is greater than a diameter of the end of the helical catheter 112 to enable the anchor 120 to remain at the end of the helical catheter 112 and the suture 116 to remain within the interior portion of the helical catheter 112 during insertion of the perianal fistula closure device (e.g., as further described herein in relation to FIG. 3B). Additionally, or alternatively, the anchor 120 may be secured to the end of the helical catheter 112 (e.g., using an adhesive, a fastener, and/or the like) to enable the anchor 120 to remain at the end of the helical catheter 112 and the suture 116 to remain within the interior portion of the helical catheter 112 during insertion of the perianal fistula closure device.

The delivery device 104 may be configured to insert the perianal fistula closure device 106 into tissue surrounding a perianal fistula. For example, an operator of the delivery device 104 may interact with a handle of the delivery device 104, or may interact with a user interface of the delivery device 104 (e.g., to engage a motor of the delivery device 104), to cause the shaft 108 to turn (e.g., in a clockwise direction). This may cause the driving component 110 to turn (e.g., in the same direction), which may cause the helical catheter 112 to insert into the tissue surrounding the perianal fistula. The insertion point 124 of the anchor 120 may facilitate insertion of the helical catheter 112 into the tissue surrounding the perianal fistula as the driving component 110 turns (e.g., by piercing the tissue to allow the helical catheter 112 to insert into the tissue to a desired depth).

The delivery device 104 may be configured to deploy the perianal fistula closure device to close the perianal fistula (e.g., after the perianal fistula closure device 106 is inserted into tissue surrounding the perianal fistula). For example, an operator of the delivery device 104 may interact with the handle of the delivery device 104, or may interact with the user interface of the delivery device 104 (e.g., to engage the motor of the delivery device 104), to cause the shaft 108 to turn (e.g., in a counter-clockwise direction). This may cause: the driving component 110 to turn (e.g., in the same direction), which may cause the anchor 120 of the perianal fistula closure device 106 to release from the helical catheter 112 and to implant in a muscle (e.g., a sphincter muscle) associated with the perianal fistula; the suture 116 of the perianal fistula closure device 106 to release from the helical catheter 112 and to distribute in a helix around an outer circumference of the perianal fistula; and the helical catheter 112 to be removed from the tissue surrounding the perianal fistula. In some implementations, the operator of the delivery device may interact with the delivery device 104 (e.g., to engage a same or different motor of the delivery device 104 described above) to cause the delivery device 104 to tighten the suture 116 as the helical catheter 112 is removed from the tissue surrounding the perianal fistula. This may cause the suture 116 to close the perianal fistula (e.g., to cause a lumen of the perianal fistula to collapse). Additionally, or alternatively, the operator of the delivery device may interact with the delivery device 104 to cause the delivery device 104 to dispense a therapeutic drug within the lumen of the perianal fistula (e.g., prior to tightening the suture 116).

In some implementations, the delivery device 104 may be configured to perform one or more additional actions (e.g., after causing the helical catheter 112 to be removed from the tissue surrounding the perianal fistula). For example, the operator of the delivery device 104 may interact with the delivery device 104 to cause the delivery device 104 to dispense a therapeutic drug, a sealant, and/or an adhesive on an opening of the perianal fistula (e.g., that is on a surface of an anal canal or a rectum). As another example, the operator of the delivery device 104 may interact with the delivery device 104 to cause the delivery device 104 to cause the cap 114 to cover the opening of the perianal fistula (e.g., thread a portion of the suture 116 that extends into the anal canal or the rectum through one or more valves of the cap 114 to cause the cap 114 to be held over the opening of the perianal fistula). In an additional example, the operator of the delivery device 104 may interact with the delivery device 104 to cause the delivery device 104 to remove (e.g., cut) a portion of the suture 116 that extends into the anal canal or the rectum (e.g., that extends past the opening of the perianal fistula and/or the cap 114).

The perianal fistula closure device 106 may be configured to close a perianal fistula (e.g., after the perianal fistula closure device is inserted in tissue surrounding the perianal fistula and deployed by the delivery device 104). In some implementations, the suture 116 may be configured to distribute around an outer circumference of the perianal fistula in a helix to close the perianal fistula (e.g., to cause a lumen of the perianal fistula to collapse). The plurality of barbs 118 of the suture 116 may be configured to secure the suture 116 in the tissue surrounding the perianal fistula. The anchor 120 may be configured to implant into a sphincter muscle associated with the perianal fistula. The plurality of quills 122 of the anchor 120 may be configured to secure the anchor 120 in the sphincter muscle.

In some implementations, the plurality of quills 122 of the anchor 120 and the plurality of barbs 118 of the suture 116 are configured to cause the suture 116 to be taut (e.g., cause the suture 116 to remain tight to ensure closure of the perianal fistula while the perianal fistula heals). As shown in FIG. 1, the plurality of quills 122 may comprise a plurality of uni-directional quills and the plurality of barbs 118 may comprise a plurality of uni-directional barbs. Accordingly, the plurality of quills 122 may be configured to secure the anchor 120 in a sphincter muscle associated with the perianal fistula and to resist movement of the anchor 120 and the suture 116 in a first direction (e.g., to resist movement in a direction that is opposite a direction of insertion of the perianal fistula closure device 106). Additionally, or alternatively, the plurality of barbs 118 may be configured to secure the suture 116 in tissue surrounding the perianal fistula and to resist movement of the suture 116 and the anchor 120 in a second direction that opposes the first direction (e.g., to resist movement in the direction of insertion of the perianal fistula closure device 106).

The cap 114 may be configured to cover an opening of the perianal fistula on a surface of an anal canal or a rectum and to prevent entry of foreign material (e.g., infectious material, such as stool) into the perianal fistula via the opening. The cap 114 may be configured to be held over the opening of the perianal fistula on the surface of the anal canal or the rectum by at least one barb (e.g., a uni-directional barb) of the plurality of barbs 118 of the suture 116. The cap 114 may comprise at least one valve (e.g., as further described herein with respect to FIG. 2) to engage with the at least one barb to cause the cap 114 to be held over the opening of the perianal fistula. In some implementations, the cap 114 may be configured to be held over the opening of the perianal fistula by an adhesive that binds the cap 114 to the surface of the anal canal or the rectum. Additionally, or alternatively, the cap 114 may be configured to be held over the opening of the perianal fistula by a sealant that creates a seal between the cap 114 and the opening of the perianal fistula and thereby prevents foreign material (e.g., infectious material, such as stool) from entering the opening of the perianal fistula and/or lodging between the cap 114 and the opening of the perianal fistula.

As indicated above, FIG. 1 is provided as an example. Other examples may differ from what is described with regard to FIG. 1.

Figure 2:
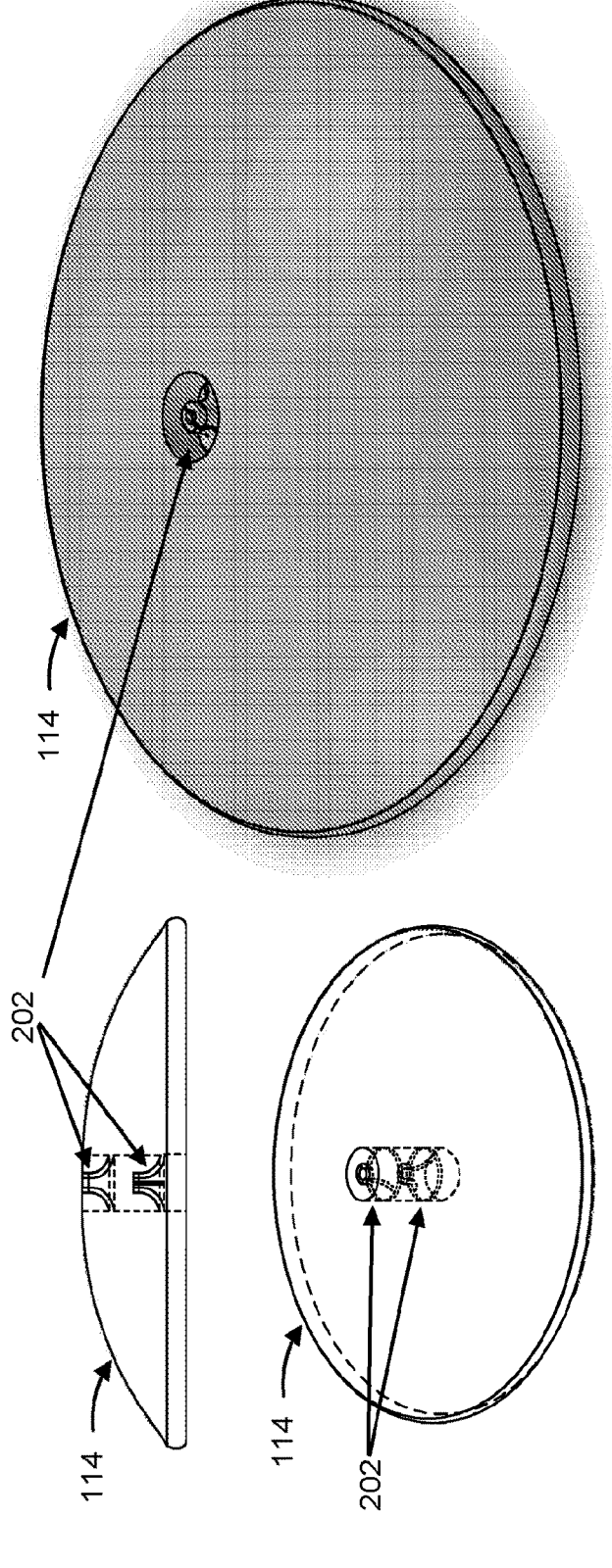
FIG. 2 is a diagram illustrating an example cap of a perianal fistula closure device described herein.

FIG. 2 is a diagram illustrating an example 200 of a cap 114 that may include one or more valves 202. The cap 114 may have a diameter that is greater than an outer diameter of a perianal fistula. For example, the cap 114 may have a diameter of 10-12 mm, which is greater than an outer diameter of typical perianal fistulas.

A valve 202 may be a one-way valve (also referred to a duck-billed valve) that is configured to allow the suture 116 to pass through an opening of the valve 202 but reduce a likelihood of entry of foreign material (e.g., infectious material, such as stool) through the opening of the valve 202. Additionally, or alternatively, the valve 202 may engage with at least one barb of the plurality of barbs 118 of the suture 116 to cause the cap 114 to be held over an opening of a perianal fistula (on a surface of an anal canal or a rectum). As further shown in FIG. 2, a plurality of valves 202 may be placed in series (e.g., one above another) to further reduce a likelihood of foreign material entering the opening of the perianal fistula via the plurality of valves 202 and to further secure the cap 114 over the opening of the perianal fistula by allowing the plurality of valves 202 to engage with one or more barbs of the plurality of barbs 118 of the suture 116.

As indicated above, FIG. 2 is provided as an example. Other examples may differ from what is described with regard to FIG. 2.

Figure 3A:
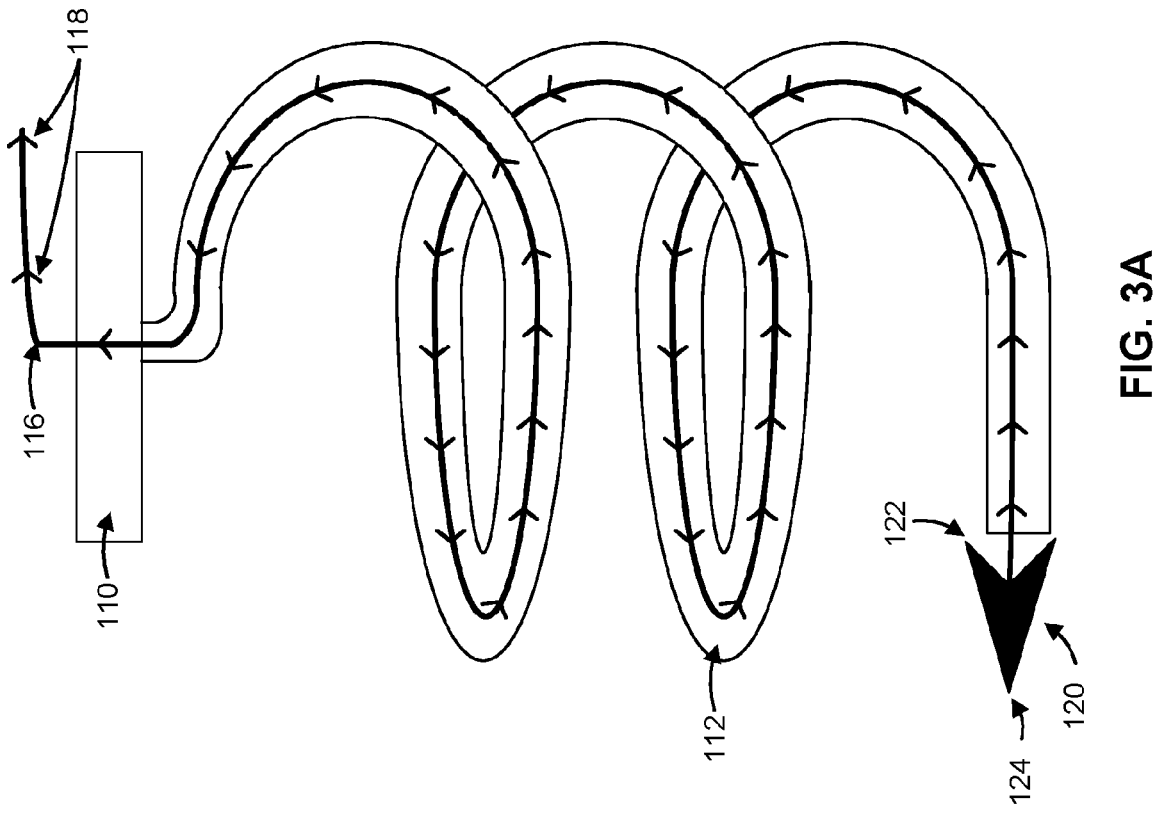
FIGS. 3A-3D are diagrams relating to an example process for inserting and deploying the perianal fistula closure device described herein.
Figure 3A:
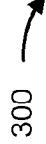

FIGS. 3A-3D are diagrams of an example 300 relating to a process for inserting and deploying the perianal fistula closure device 106 using the delivery device 104. As shown in FIG. 3A, prior to insertion or deployment of the perianal fistula closure device 106, the helical catheter 112 of the delivery device 104 may hold the suture 116 within an interior portion of the of the helical catheter 112 and may hold the anchor 120 at an end of the helical catheter 112. An additional end of the helical catheter 112 may be connected to the driving component 110 of the delivery device 104. An end of the suture 116 (e.g., that is not connected to the anchor 120) may pass through the driving component and may extend into an anal canal or a rectum.

In preparation of inserting the perianal fistula closure device 106, an operator of the delivery device (e.g., a surgeon) may use the perianal fistula debriding device 102 to clean and/or debride a perianal fistula (e.g., to remove epithelial tissue in a tract of the perianal fistula and/or to expose fresh tissue on the interior of the tract) and/or to stimulate healing of the perianal fistula (e.g., to damage tissue associated with the perianal fistula, which stimulates healing of the tissue and thereby promotes growth of the tissue to close the perianal fistula). The operator may also use a probe to locate an opening of the perianal fistula (e.g., that is on a surface of an anal canal or a rectum).

Figure 3B:
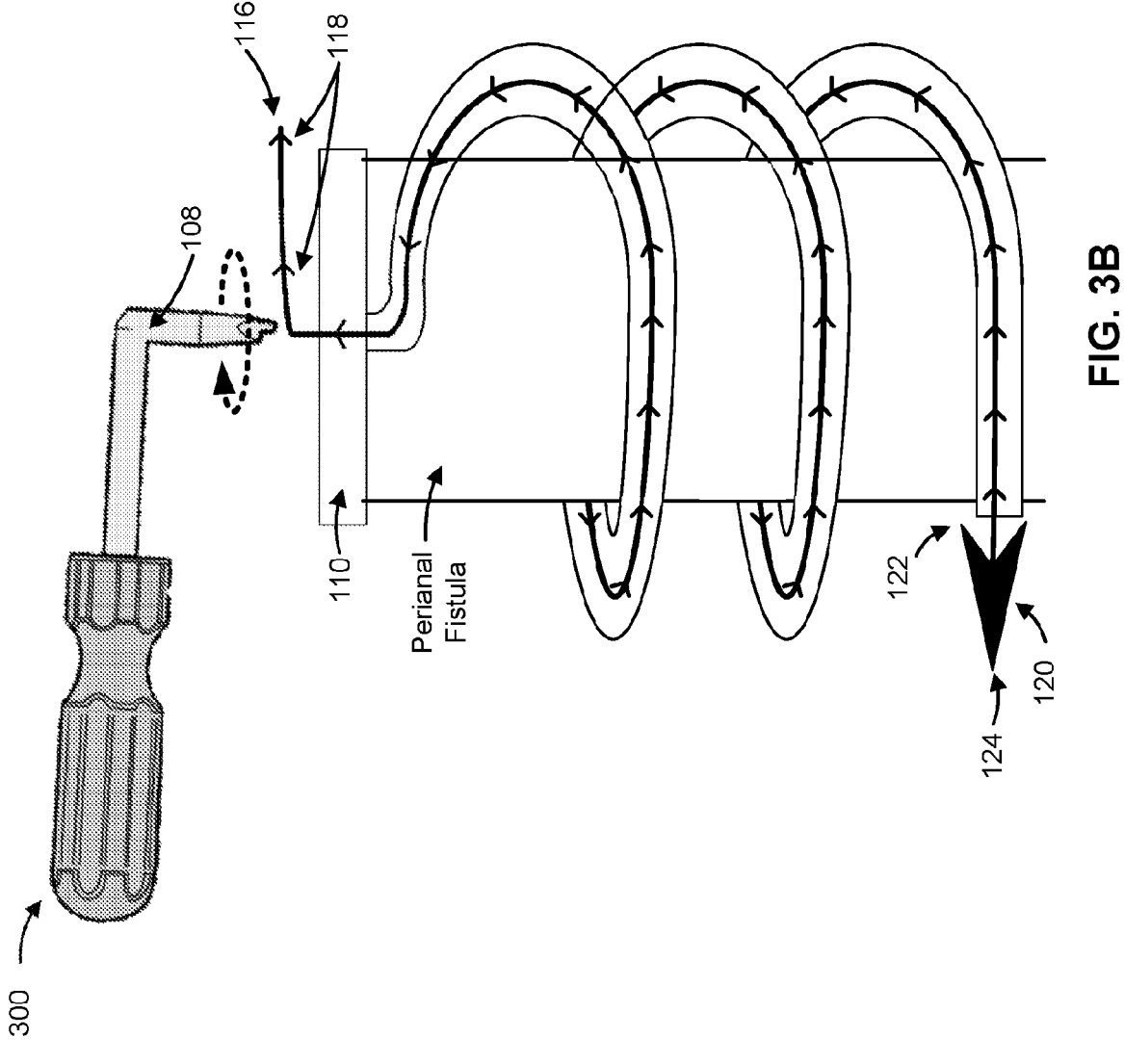

After the operator locates the opening of the perianal fistula, the operator may use the delivery device 104 to insert the perianal fistula closure device 106 into tissue surrounding the perianal fistula. As shown in FIG. 3B, the operator may place the delivery device 104 (e.g., that is holding the perianal fistula closure device 106) on the opening of the perianal fistula and may interact with the delivery device 104 (e.g., to engage a motor of the delivery device 104), to cause the shaft 108 of the delivery device 104 to turn (e.g., in a clockwise direction), which causes the driving component 110 to turn (e.g., in the same direction). This may cause the helical catheter 112 to insert into the tissue surrounding the perianal fistula. The insertion point 124 of the anchor 120 may facilitate insertion of the helical catheter 112 into the tissue surrounding the perianal fistula as the driving component 110 turns (e.g., by piercing the tissue to allow the helical catheter 112 to insert into the tissue to a desired depth, such as 8 to 12 mm). Accordingly, the helical catheter 112 may drive the suture 116 circumferentially around a proximal portion of the perianal fistula, so that the suture 116 surrounds the perianal fistula with a margin (e.g., of at least 2-3 mm) in all directions around the perianal fistula. The helical catheter 112, the suture 116, and/or the anchor 120 may be driven circumferentially through an internal anal sphincter muscle and/or an intersphincteric plane, and the anchor 120 may be implanted in a proximal portion of an external anal sphincter muscle.

Figure 3C:
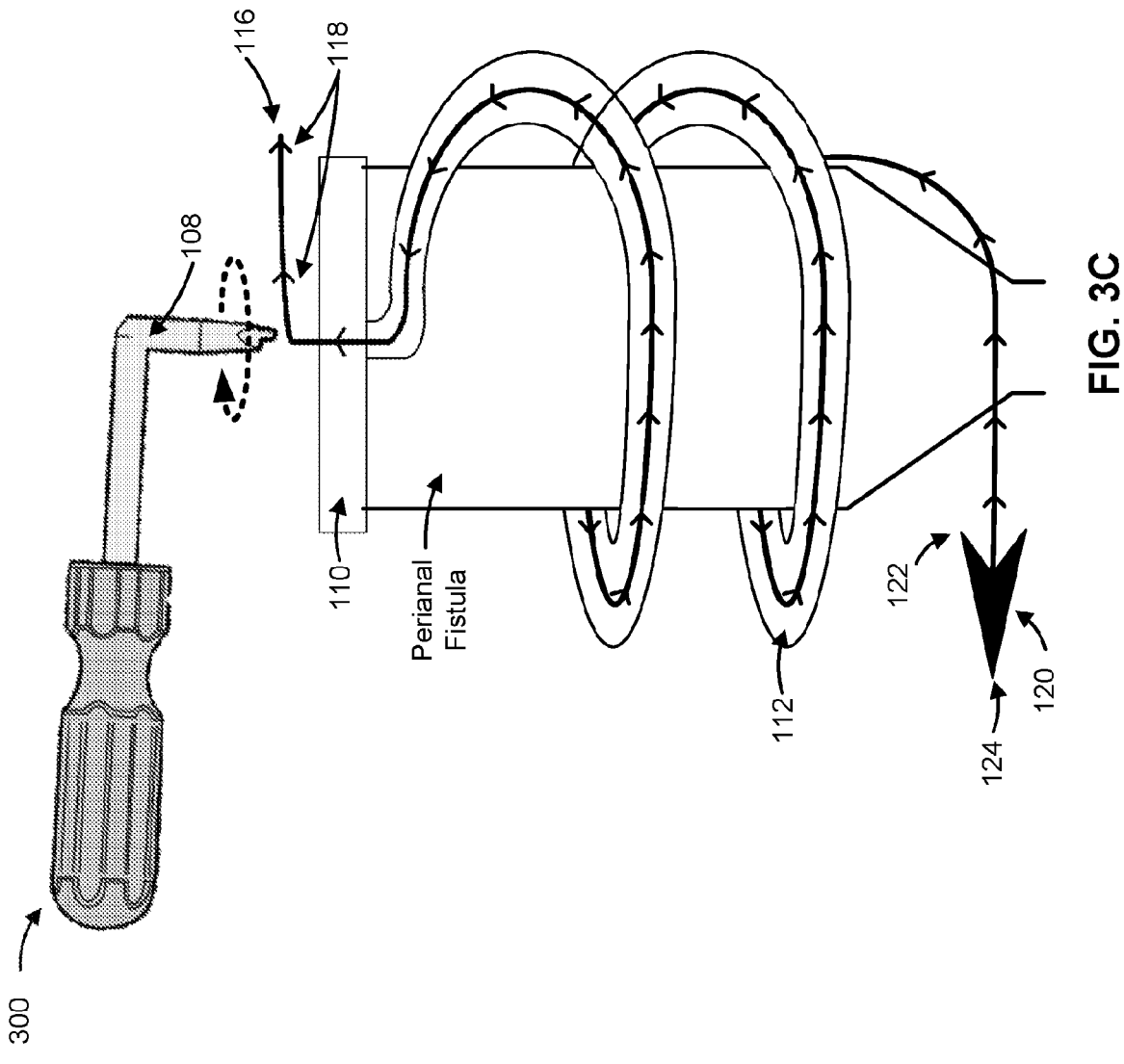

After the perianal fistula closure device 106 is inserted into the tissue surrounding the perianal fistula, the operator may use the delivery device 104 to deploy the perianal fistula closure device to close the perianal fistula. As shown in FIG. 3C, the operator may interact with the delivery device 104 (e.g., to engage a motor of the delivery device 104), to cause the shaft 108 of the delivery device 104 to turn (e.g., in a counter-clockwise direction), which causes the driving component 110 to turn (e.g., in the same direction). This may cause the helical catheter 112 to be removed from the tissue surrounding the perianal fistula (e.g., one loop at a time). This may also cause the anchor 120 and the suture 116 of the perianal fistula closure device 106 to release from the helical catheter 112. In some implementations, the operator of the delivery device 104 may interact with the delivery device 104 (e.g., to engage a same or different motor of the delivery device 104 described above) to cause the delivery device 104 to tighten the suture 116 as the helical catheter 112 is removed from the tissue surrounding the perianal fistula (e.g., as the helical catheter 112 is removed one loop at a time). This may cause the suture 116 to close the perianal fistula (e.g., to cause a lumen of the perianal fistula to collapse). For example, as the suture 116 is tightened during a first "bite" shown in FIG. 3C, the anchor 120 may actuate such that the plurality of quills 122 flay outwards and implant in external anal sphincter muscle tissue. Securing in this tissue plane ensures a strong point of tension for the suture 116 to be able to successfully deploy and approximate a remaining length of the perianal fistula. This process may be repeated until the helical catheter 112 is fully removed (e.g., one loop at a time) from the tissue surrounding the perianal fistula.

Figure 3D:
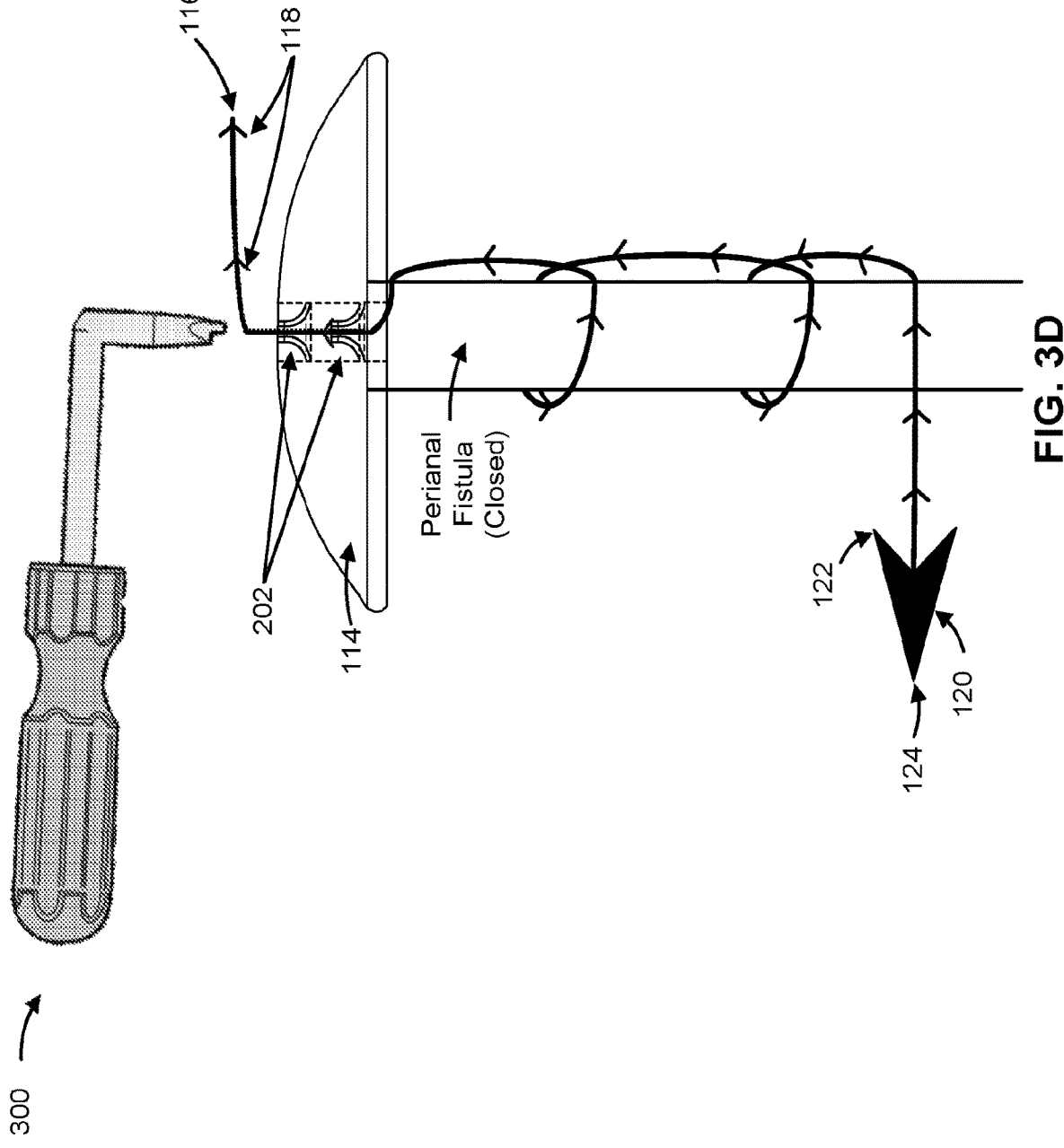

Turning to FIG. 3D, after the perianal fistula closure device 106 is deployed, the perianal fistula may be closed (e.g., the suture 116 may tighten around the perianal fistula to cause a lumen of the perianal fistula to collapse). In some implementations, the operator of the delivery device 104 may interact with the delivery device 104 to cause the delivery device 104 to cause the cap 114 to cover the opening of the perianal fistula (e.g., to thread a portion of the suture 116 that extends into the anal canal or the rectum through the one or more valves 202 of the cap 114 to cause the cap 114 to be held over the opening of the perianal fistula). The delivery device 104 may tightly cinch the cap over the opening of the perianal fistula to allow at least one barb of the plurality of barbs 118 to engage with the one or more valves 202 to cause the cap to be held over the opening of the perianal fistula. In some implementations, the operator of the delivery device 104 may interact with the delivery device 104 to cause the delivery device 104 to remove (e.g., cut using a cutting implement of the delivery device 104, such as surgical scissors) a portion of the suture 116 that extends into the anal canal or the rectum (e.g., that extends past the opening of the perianal fistula and/or the cap 114).

After a period of time, the suture 116 and/or the anchor 120 may dissolve or may be absorbed by the tissue surrounding the perianal fistula. For example, when the suture 116 and the anchor 120 comprise polydioxanone (e.g., that has a tensile strength of 4.89 kilogram-force (kgf)), the suture 116 and the anchor 120 may dissolve or may be absorbed after 180 days, and may reach 50% tensile strength after 28-42 days. This allows for primary healing of the perianal fistula to occur over a 4-6 week period after deployment of the perianal fistula closure device 106, which decreases a likelihood of recurrence of the perianal fistula. After the suture 116 and/or the anchor 120 loses a majority of tensile strength, the cap 114 may release from the surface of the anal canal or the rectum and may be expelled from the anal canal or the rectum (e.g., in association with a bowel movement).

As indicated above, FIGS. 3A-3D are provided as an example. Other examples may differ from what is described with regard to FIGS. 3A-3D.

The foregoing disclosure provides illustration and description, but is not intended to be exhaustive or to limit the implementations to the precise forms disclosed. Modifications and variations may be made in light of the above disclosure or may be acquired from practice of the implementations.

Certain user interfaces have been described herein. A user interface may include a graphical user interface, a nongraphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

10

What is claimed is:
1. A system, comprising:
a delivery device configured to deploy a perianal fistula closure device, comprising:
a helical catheter; and
the perianal fistula closure device configured to close a perianal fistula, comprising:
a cap,
a suture comprising a plurality of uni-directional barbs that are configured in a first direction and configured to resist movement in a direction of insertion of the perianal fistula closure device, and
an anchor connected to an end of the suture comprising a plurality of uni-directional quills that are configured in a second direction opposite to the first direction, and configured to resist movement in a direction that is opposite to the direction of insertion of the perianal fistula closure device.
2. The system of claim 1, further comprising a perianal fistula debriding device that is configured to debride the perianal fistula.
3. The system of claim 1, wherein the delivery device further comprises:
a shaft; and
a driving component connected to an end of the shaft, wherein the helical catheter is connected to the driving component.
4. The system of claim 1, wherein the delivery device is configured to:
insert the perianal fistula closure device in tissue surrounding the perianal fistula; and
deploy the perianal fistula closure device to cause the perianal fistula to close.
5. The system of claim 1, wherein the suture is configured to, after the perianal fistula closure device is deployed by the delivery device, distribute around an outer circumference of the perianal fistula in a helix to collapse a lumen of the perianal fistula.
6. The system of claim 1, wherein the plurality of uni-directional quills of the anchor and the plurality of uni-directional barbs of the suture are configured to, after the perianal fistula closure device is deployed by the delivery device, cause the suture to be taut,
wherein causing the suture to be taut facilitates closure of the perianal fistula.
7. The system of claim 1, wherein the anchor is configured to implant into a sphincter muscle associated with the perianal fistula and the plurality of uni-directional quills of the anchor is configured to secure the anchor in the sphincter muscle.
8. The system of claim 1, wherein the cap is configured to cover an opening of the perianal fistula on a surface of an anal canal or a rectum and to prevent entry of foreign material into the perianal fistula via the opening.
9. A perianal fistula closure device configured to close a perianal fistula, comprising:
a cap;
a suture comprising a plurality of uni-directional barbs that are configured in a first direction and configured to resist movement in a direction of insertion of the perianal fistula closure device; and
an anchor connected to an end of the suture comprising a plurality of uni-directional quills that are configured in a second direction opposite to the first direction, and configured to resist movement in a direction that is opposite to the direction of insertion of the perianal fistula closure device.

10. The perianal fistula closure device of claim 9, wherein at least one of the suture or the anchor comprises a biocompatible material or bioabsorbable material.

11. The perianal fistula closure device of claim 9, wherein the plurality of uni-directional barbs of the suture is configured to secure the suture in tissue surrounding the perianal fistula.

12. The perianal fistula closure device of claim 9, wherein the cap is configured to be held over an opening of the perianal fistula on a surface of an anal canal or a rectum by at least one uni-directional barb of the plurality of uni-directional barbs of the suture.

13. The perianal fistula closure device of claim 12, wherein the cap comprises at least one valve to engage with the at least one uni-directional barb to cause the cap to be held over the opening of the perianal fistula.

14. The perianal fistula closure device of claim 9, wherein the cap is configured to be held over an opening of the perianal fistula on a surface of an anal canal or a rectum by at least one of:

at least one uni-directional barb of the plurality of uni-directional barbs of the suture; or an adhesive that binds the cap to the surface of the anal canal or the rectum.

15. The perianal fistula closure device of claim 9, wherein the cap comprises a plurality of valves, wherein a valve of the plurality of valves is configured to engage with at least one barb of the plurality of uni-directional barbs to cause the cap to be held over an opening of the perianal fistula.

16. A device, comprising:

a perianal fistula closure device comprising:

a cap;

a suture comprising a plurality of uni-directional barbs that are configured in a first direction and configured to resist movement in a direction of insertion of the perianal fistula closure device; and an anchor connected to an end of the suture comprising a plurality of uni-directional quills that are configured in a second direction opposite to the first direction, and configured to resist movement in a direction that is opposite to the direction of insertion of the perianal fistula closure device; and a delivery device comprising:

a driving component; and a helical catheter connected to the driving component, wherein, the helical catheter is configured to, prior to the delivery device deploying the perianal fistula closure device:

hold the suture of the perianal fistula closure device within an interior portion of the helical catheter, and hold the anchor of the perianal fistula closure device at an end of the helical catheter such that an insertion point of the anchor protrudes from the end of the helical catheter.

17. The device of claim 16, wherein the delivery device is configured to, when inserting the perianal fistula closure device into tissue associated with a perianal fistula:

cause the driving component to turn; and cause, based on a turning motion of the driving component, the helical catheter to insert into the tissue surrounding the perianal fistula, wherein an insertion point of the anchor facilitates insertion of the helical catheter into the tissue surrounding the perianal fistula as the driving component turns.

18. The device of claim 16, wherein the delivery device is configured to, when deploying the perianal fistula closure device:

cause, based on a turning motion of the driving component:

the anchor of the perianal fistula closure device to release from the helical catheter and to implant in a muscle associated with the perianal fistula;

the suture of the perianal fistula closure device to release from the helical catheter and to distribute in a helix around an outer circumference of the perianal fistula; and the helical catheter to be removed from tissue associated with the perianal fistula.

19. The device of claim 18, wherein the delivery device is configured to, when causing the helical catheter to be removed from the tissue associated with the perianal fistula:

cause the suture of the perianal fistula closure device to be tightened as the helical catheter is removed, wherein causing the suture to be tightened causes a lumen of the perianal fistula to collapse.

20. The device of claim 19, wherein the delivery device is further configured to:

cause a therapeutic drug to be dispensed within the lumen of the perianal fistula prior to causing the lumen of the perianal fistula to collapse.

21. The device of claim 18, wherein the delivery device is further configured to, after causing the helical catheter to be removed from the tissue associated with the perianal fistula, at least one of:

cause a therapeutic drug to be dispensed on an opening of the perianal fistula that is on a surface of an anal canal or a rectum;

cause the cap of the perianal fistula closure device to cover the opening of the perianal fistula; or cause a portion of the suture of the perianal fistula closure device that extends into the anal canal or the rectum to be removed.

* * * * *